(12) United States Patent
Kimura et al.

(10) Patent No.: US 7,655,814 B2
(45) Date of Patent: Feb. 2, 2010

(54) PROCESS FOR PRODUCING CROCONIC ACID OR SALT THEREOF

(75) Inventors: Keizou Kimura, Odawara (JP); Katsuyoshi Yamakawa, Odawara (JP)

(73) Assignee: Fujifilm Corporation, Tokyo (JP)

( * ) Notice: Subject to any disclaimer, the term of this patent is extended or adjusted under 35 U.S.C. 154(b) by 308 days.

(21) Appl. No.: 11/394,109

(22) Filed: Mar. 31, 2006

(65) Prior Publication Data

US 2006/0224022 A1 Oct. 5, 2006

(30) Foreign Application Priority Data

Mar. 31, 2005 (JP) ............................ 2005-101914

(51) Int. Cl.
*C07C 253/00* (2006.01)
(52) U.S. Cl. .................................................. 558/364
(58) Field of Classification Search ................... 558/364
See application file for complete search history.

(56) References Cited

U.S. PATENT DOCUMENTS 2,815,314 A 12/1957 Hale et al.

OTHER PUBLICATIONS

Fornals et al. CAS: 109:231221, 1987.*
O. Gelormini, et al., "The Oxidation of Inosite with Nitric Acid", Journal of the American Chemical Society (1930), vol. 52, pp. 2483-2494.
Jack D. Knight et al.; J. Am. Chem. Soc., vol. 73, pp. 4136-4138, 1951.
Singh Bharat et al.; Tetrahedron, vol. 41, No. 14, pp. 2871-2874, 1985.
Shoji Kajigaeshi et al.; Bull. Chem. Soc. of Japan; vol. 62, No. 8, pp. 2585-2588, 1989.

* cited by examiner

*Primary Examiner*—Rei-tsang Shiao
(74) *Attorney, Agent, or Firm*—Birch, Stewart, Kolasch & Birch, LLP

(57) ABSTRACT

Croconic acid or a salt thereof is easily produced at low cost by a reaction of a hydrocarbon compound consisting of a five-membered ring or a hydrocarbon compound consisting of a five-membered ring having an oxo group and/or a monovalent group linked via an oxygen atom with a halogenating agent.

5 Claims, No Drawings

PROCESS FOR PRODUCING CROCONIC ACID OR SALT THEREOF

BACKGROUND OF THE INVENTION

1. Field of the Invention

The present invention relates to a process for producing croconic acid (i.e., 4,5-dihydroxy-4- cyclopentene-1,2,3-trione) or a salt thereof.

2. Description of the Related Art

Croconic acid or a salt thereof is useful as a dye, a medicine, an agricultural chemical and the like, or as an intermediate thereof (see, for example, JP-A-2001-294785, JP-A-2001-117201 and JP-A-5-155145). As a related synthetic method for such a compound, for example, it is known that croconic acid is present in a reaction mixture formed by the oxidation of inositol with fuming nitric acid (see Journal of the American Chemical Society Vol. 52, p. 2483 (1930)), or a metal salt of croconic acid is obtained by performing oxidative decarboxylation of tetrahydroxybenzoquinone obtained through two steps from chloranil (see Chemical World, Vol. 3, p 139 (1999)). However, there has been a demand for the development of an inexpensive and simple process for producing croconic acid or a salt thereof.

SUMMARY OF THE INVENTION

An object of the present invention is to provide an inexpensive and simple process for producing croconic acid and a salt thereof.

The present inventors have made intensive studies, and as a result, they found that by a production process described below, the above object can be achieved.

(1) A process for producing croconic acid or a salt thereof comprising reacting a hydrocarbon compound consisting of a five-membered ring or a hydrocarbon compound consisting of a five-membered ring having an oxo group and/or a monovalent group linked via an oxygen atom with a halogenating agent.

(2) The process for producing croconic acid or a salt thereof according to (1), wherein the reaction is carried out in the presence of a base.

(3) The process for producing croconic acid or a salt thereof according to (1) or (2), wherein the five-membered ring has a carbon-carbon double bond.

(4) The process for producing croconic acid or a salt thereof according to any one of (1) to (3), wherein the reaction is carried out in the co-presence of water.

(5) The process for producing croconic acid or a salt thereof according to any one of (1) to (4), wherein a salt of croconic acid produced in the reaction system is neutralized with an acid thereby forming croconic acid.

According to the production process of the present invention, croconic acid and a salt thereof, which are useful as a dye, a medicine, an agricultural chemical and the like, or as an intermediate thereof, can be produced simply and at low cost.

BEST MODE FOR CARRYING OUT THE INVENTION

Hereinafter, a production process of the present invention will be described in detail. The description of the following constituting requirements will be made based on a representative embodiment of the present invention, however, the present invention is not limited to such an embodiment. In the present specification, ranges indicated with "to" mean ranges including the numerical values before and after "to" as the minimum and maximum values respectively.

The hydrocarbon ring in a hydrocarbon compound consisting of a five-membered ring or a hydrocarbon compound consisting of a five-membered ring having an oxo group and/or a monovalent group linked via an oxygen atom to be used in the present invention may contain only carbon-carbon single bonds or may contain a carbon-carbon double bond. Examples of the five-membered ring constituting such a hydrocarbon compound include cyclopentane, and cyclopentene, cyclopentadiene and the like. Among these, cyclopentadiene may be used in reaction as a compound obtained by reacting dicyclopentadiene either in the reaction system or outside the reaction system. Preferred rings are cyclopentene and cyclopentadiene, and most preferred ring is cyclopentene.

Such a ring may have an oxo group and/or a monovalent group linked via an oxygen atom, and in the present invention, it is preferred to use a compound consisting of such a ring having a substituent. Examples of the monovalent group linked via an oxygen atom include a hydroxyl group, an alkoxy group (preferred is an alkoxy group having 1 to 4 carbon atoms, and examples thereof include a methoxy group, an ethoxy group, a butoxy group), an acyloxy group (preferred is an acyloxy group having 0 to 5 carbon atoms, and examples thereof include a formyloxy group, an acetyloxy group, a butane carbonyloxy group), and a sulfonyloxy group (preferred is a sulfonyloxy group having 1 to 7 carbon atoms and examples thereof include a methanesulfonyloxy group, a benzenesulfonyloxy group, a toluenesulfonyloxy group). Among these, a hydroxyl group and an alkoxy group are preferred, and a hydroxyl group is further preferred.

The ring may have 1 to 3 oxo groups, or 1 to 3 monovalent groups linked via an oxygen atom (particularly preferably a hydroxyl group), or may have both at least one oxo group and at least one monovalent group linked via an oxygen atom. Examples of the ring having such a substituent include cyclopentanol, 1,2-cyclopentanediol, 1,3-cyclopentanediol, cyclopentanone, 1,3-cyclopentanedione, 1,2-cyclopentanedione, 1,2,4-cyclopentanetrione, 3-cyclopentene-1,2-dione, 2,4-cyclopentadiene-1-one, 2-cyclopentene-1-one, 4-cyclopentene-1,3-dione, 3-methoxy-2-cyclopentene-1-one and the like. Among these, preferred are cyclopentanone, 1,3-cyclopentane-dione, 1,2,4-cyclopentanetrione, 2-cyclopentene-1-one and 4-cyclopentene-1,3-dione, and further preferred are 1,3-cyclopentanedione and 4-cyclopentene-1,3-dione.

As a halogenating agent to be used in the present invention, an inorganic or organic halogenating agent can be used, and these can be used alone or in combination.

Examples of the inorganic halogenating agent include chlorine, bromine, iodine, phosphorous trichloride, phosphorous pentachloride, phosphorus tribromide, sulfuryl oxide, sodium chlorate and the like.

Examples of the organic halogenating agent include trichloroisocyanuric acid, N-chlorosuccinimide, 1,3-dichloro-5,5-dimethylhydantoin, 1,3-dibromo-5,5- dimethylhydantoin and the like.

Among these, preferred are chlorine, bromine, iodine, sulfuryl oxide, sodium chlorate, trichloroisocyanuric acid, 1,3-dichloro-5,5-dimethylhydantoin and 1,3- dibromo-5,5-dimethylhydantoin, more preferred are chlorine, bromine, sulfuryl oxide, sodium chlorate, trichloroisocyanuric acid and 1,3-dichloro-5,5- dimethylhydantoin, further more preferred are chlorine, bromine and trichloroisocyanuric acid, and most preferred is chlorine or bromine.

Then, a production process of the present invention will be described.

The production process of the present invention comprises reacting the above-mentioned hydrocarbon compound consisting of a five-membered ring or hydrocarbon compound consisting of a five-membered ring having an oxo group and/or a monovalent group linked via an oxygen atom with a halogenating agent.

The theoretical amount of the halogenating agent to be used is determined depending on the type of the above-mentioned five-membered ring compound, particularly the oxidation stage of the compound. However, it is preferably 1 to 3 equivalent amount, more preferably 1 to 2 equivalent amount, and further more preferably 1 to 1.5 equivalent amount based on the theoretical amount.

In the present invention, it is preferred to use a base.

As the base, an inorganic or organic base can be used. As the inorganic base, a hydroxide, carbonate or bicarbonate of a metal or the like is preferred. Specific examples thereof include lithium hydroxide, sodium hydroxide, potassium hydroxide, magnesium hydroxide, calcium hydroxide, barium hydroxide, cesium hydroxide, sodium carbonate, potassium carbonate, magnesium carbonate, calcium carbonate, barium carbonate, cesium carbonate, sodium bicarbonate, potassium bicarbonate and the like. Examples of the organic base include aromatic, aliphatic, and heterocyclic amines. Specific examples thereof include pyridine, α-picoline, γ-picoline, piperidine, triethylamine, 1,4-azabicyclo[2.2.2]octane, 1,8-diazabicyclo[5.4.0]-7-undecene and the like.

The amount of such a base to be used is preferably 0 to 4 equivalent amount, more preferably 1 to 3 equivalent amount, and further more preferably 1 to 2 equivalent amount based on the halogenating agent.

As a reaction solvent, water, an amide-based solvent (such as N,N-dimethylformamide, N,N-dimethylacetoamide, 1-methyl-2-pyrrolidinone or 1,3-imidazolidinone), a sulfone-based solvent (such as sulforane), a sulfoxide-based solvent (such as dimethylsulfoxide), an ether-based solvent (such as dioxane), a ketone-based solvent (such as acetone or cyclohexanone), a hydrocarbon-based solvent (such as toluene, xylene, n-hexane or n-octane), a halogen-based solvent (such as tetrachloroethane, dichloromethane, carbon tetrachloride, 1,2-dichloroethane or chlorobenzene), an alcohol-based solvent (such as methanol, ethanol, ethylene glycol, glycerol or phenol), a nitryl-based solvent (such as acetonitryl), an amine-based solvent (such as triethylamine, pyrrolidine, pyridine or picoline) can be used alone or in combination.

Among these, preferred are water, a hydrocarbon-based solvent, a halogen-based solvent, a nitryl-based solvent and an amine-based solvent, more preferred are water, a hydrocarbon-based solvent, a halogen-based solvent and an amine-based solvent, and further more preferred are water and a halogen-based solvent.

In the present invention, it is preferred to perform the reaction in the presence of water in order to ensure the fluidity when production is performed by dissolving a raw material or an inorganic substance of a reaction by-product. At this time, it is also preferred to use any of the above-mentioned solvents in combination.

The amount of the reaction solvent to be used can vary depending on the industrial scale and is not particularly limited, as long as it does not cause a problem in the steps such as a difficulty in stirring. However, in terms of economic efficiency and improvement of reactivity, it is preferably 0.1 to 1000 masses, more preferably 0.5 to 300 masses, and particularly preferably 5 to 50 masses per one mass of the five-membered ring compound that is a raw material.

The reaction temperature is preferably in the range from −30 to 200° C., more preferably from 0 to 150° C., and further more preferably from 20 to 100° C. The reaction time is preferably in the range from 5 minutes to 10 hours and more preferably from 30 minutes to 3 hours. In addition, it is also preferred that the reaction is performed at 0 to 20° C. for 30 minutes to 5 hours and then the reaction temperature is raised and the reaction is performed for an additional 30 minutes to 5 hours at 40 to 100° C.

As for the reaction, a method in which the halogenating agent is added to a mixture containing the five-membered ring compound that is a raw material and the base is preferred. In addition, a method in which the halogenating agent is added to the five-membered ring compound that is a raw material and then the base is added thereto is also preferred.

In the case where a salt of croconic acid is obtained by the reaction, it is preferred that the salt is neutralized with an organic or an inorganic acid thereby obtaining the product as croconic acid. As the acid to be used, an inorganic acid is preferred, and hydrochloric acid and sulfuric acid are more preferred.

EXAMPLES

The features of the present invention will be more specifically described with reference to the following Examples and Comparative Examples. The materials, amounts, ratios, processes, procedures and the like shown in the following Examples can be optionally changed as long as such a change does not depart from the spirit of the present invention. Therefore, the scope of the present invention should not be construed as being limited by the following specific examples.

Example 1

Croconic acid was synthesized based on the following reaction formula.

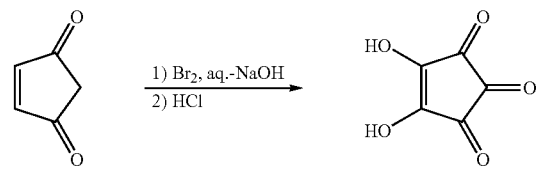

A solution composed of 108 g of sodium hydroxide and 300 ml of water was added to a three-neck flask, and 14.4 g of 2-cyclopentene-1,4-dione was added thereto while the solution was stirred under ice cooling. Subsequently, 144 g of bromine was added dropwise thereto over a period of 40 minutes. The inner temperature was 10 to 20° C. during the dropwise addition. After the completion of the dropwise addition, the ice bath was removed, and the solution was stirred as such for 1 hour. Then, 110 g of hydrogen chloride was passed into the solution under ice cooling, and the precipitated crystal was separated by filtration. The filtrate was concentrated with a rotary evaporator. Then, 500 ml of methanol was added to the residue and the solution was stirred and filtered. The resulting filtrate was concentrated with a rotary evaporator, and the residue was recrystallized with water, whereby 18.8 g of the objective croconic acid was obtained.

Yield: 88%

$^1$H-NMR (D$_2$O): δ=11.621 (brs, 2H)

Example 2

A solution composed of 108 g of sodium hydroxide and 300 ml of water was added to a three-neck flask, and 14.4 g of 2-cyclopentene-1,4-dione was added thereto while the solution was stirred under ice cooling. Subsequently, 144 g of bromine was added dropwise thereto over a period of 40 minutes. The inner temperature was 10 to 20° C. during the dropwise addition. After the completion of the dropwise addition, the ice bath was removed, and the solution was stirred as such for 1 hour. Then, the precipitated crystal was separated by filtration. The filtrate was concentrated with a rotary evaporator. Then, 500 ml of methanol was added to the residue and the solution was stirred and filtered. The resulting filtrate was concentrated with a rotary evaporator, and the residue was recrystallized with water, whereby 21.2 g of the objective sodium croconate was obtained.

Yield: 76%

Example 3

Croconic acid was synthesized based on the following reaction formula.

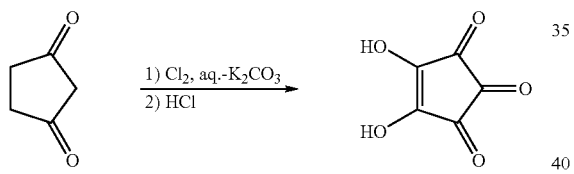

To a three-neck flask, 165.9 g of potassium carbonate and 300 ml of water were added, and 9.81 g of cyclopentane-1,3-dione was added thereto while the solution was stirred under ice cooling. Subsequently, 56.8 g of chlorine was passed into the solution while the inner temperature was maintained at 15° C. or lower, and the solution was stirred as such for 3 hours. Thereafter, the solution was stirred at an inner temperature of 50° C. for 3 hours in a hot water bath. Then, the inner temperature was lowered to 10° C. under ice cooling, and 91.3 g of hydrogen chloride was passed into the solution, and the precipitated crystal was separated by filtration. The filtrate was concentrated with a rotary evaporator, and methanol was added to the residue to dissolve it. Then, the solution was filtered, and the resulting filtrate was concentrated with a rotary evaporator. The resulting residue was recrystallized with water, whereby 9.39 g of the objective croconic acid was obtained.

Yield: 66%

Example 4

Croconic acid was synthesized based on the following reaction formula.

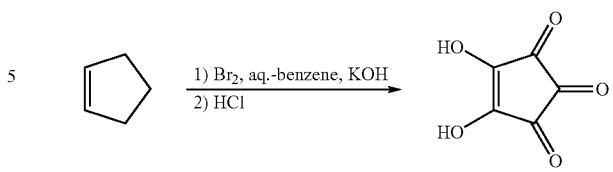

To a three-neck flask, 140 g of potassium hydroxide and 300 ml of water were added, and the potassium hydroxide was dissolved by stirring the solution, and then 100 ml of benzene was added thereto. While the solution was stirred under ice cooling, 6.81 g of cyclopentene was added thereto, and while the inner temperature was maintained at 20° C. or lower, 192 g of bromine was added dropwise thereto. After the completion of the dropwise addition, the solution was stirred as such for 1 hour, and then the ice bath was removed and the solution was stirred for an additional 2 hours. Thereafter, the solution was stirred while heating at an inner temperature of 60° C. for 2 hours. Then, the inner temperature was lowered to 5° C. under ice cooling, and 110 g of hydrogen chloride was passed into the solution. The precipitated crystal was separated by filtration, and the resulting filtrate was concentrated with a rotary evaporator. Then, 100 ml of methanol was added to the residue to dissolve it. This solution was filtered and the filtrate was concentrated with a rotary evaporator. The resulting residue was recrystallized with water, whereby 11.8 g of the objective croconic acid was obtained.

Yield: 83%

Example 5

Croconic acid was synthesized based on the following reaction formula.

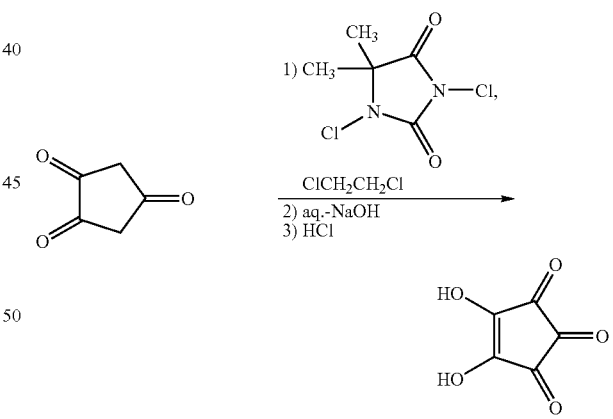

To a three-neck flask, 11.2 g of cyclopentane-1,2,4-trione and 400 ml of 1,2-dichloroethane were added, and 98.5 g of 2,4-dichloro-5,5-dimethylhydantoin was added thereto over a period of 60 minutes while the solution was stirred under ice cooling. The ice bath was removed, and the solution was stirred as such for 1 hour, and then a solution composed of 48 g of sodium hydroxide and 100 ml of water was added dropwise thereto over a period of 30 minutes under ice cooling. Then, the ice bath was removed and the solution was stirred as such for 1 hour. Thereafter, the solution was stirred while heating at an inner temperature of 50° C. for 3 hours. Then, 44 g of hydrogen chloride was passed into the solution under ice cooling, and the precipitated crystal was separated by filtration. The resulting filtrate was concentrated with a rotary evaporator, and then methanol was added to the residue to dissolve it. This solution was filtered and the filtrate was concentrated with a rotary evaporator. The resulting residue was recrystallized with water, whereby 8.97 g of the objective croconic acid was obtained.

Yield: 63%

According to the production process of present invention, croconic acid and a salt thereof can be produced simply and at low cost. Croconic acid and a salt thereof are useful as a dye, a medicine, an agricultural chemical and the like, and moreover, it can be used as a synthetic intermediate thereof, therefore, the present invention has high industrial applicability.

The present disclosure relates to the subject matter contained in Japanese Patent Application No. 101914/2005 filed on Mar. 31, 2005, which is expressly incorporated herein by reference in its entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A process for producing croconic acid or a salt thereof comprising
reacting a hydrocarbon compound consisting of a five-membered ring having an oxo group and/or a monovalent group linked via an oxygen atom selected from the group consisting of cyclopentanol, 1,2-cyclopentanediol, 1,3-cyclopentanediol, cyclopentanone, 1,3-cyclopentanedione, 1,2-cyclopentanedione, 1,2,4-cyclopentanetrione, 3-cyclopentene-1,2-dione, 2,4-cyclopentadiene-1-one, 2-cyclopentene-1-one, 4-cyclopentene-1,3-dione and 3-methoxy-2-cyclopentene-1-one
with a halogenating agent.

2. The process for producing croconic acid or a salt thereof according to claim 1, wherein the reaction is carried out in the presence of a base.

3. The process for producing croconic acid or a salt thereof according to claim 1, wherein the reaction is carried out in the co-presence of water.

4. The process for producing croconic acid or a salt thereof according to claim 1, wherein a salt of croconic acid produced in the reaction system is neutralized with an acid thereby forming croconic acid.

5. The process for producing croconic acid or a salt thereof according to claim 1, wherein the halogenating agent is selected from the group consisting of chlorine, bromine, iodine, phosphorous trichlonde, phosphorous pentachloride, phosphorus tribromide, sulfuryl oxide, sodium chlorate, trichloroisocyanuric acid, N-chlorosuccinimide, 1,3-dichloro-5,5-dimethylhydantoin, and 1,3-dibromo-5,5-dimethylhydantoin.

* * * * *

UNITED STATES PATENT AND TRADEMARK OFFICE
CERTIFICATE OF CORRECTION

PATENT NO. : 7,655,814 B2
APPLICATION NO. : 11/394109
DATED : February 2, 2010
INVENTOR(S) : Kimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 610 days.

Signed and Sealed this

Twenty-third Day of November, 2010

David J. Kappos
*Director of the United States Patent and Trademark Office*